United States Patent
Lim et al.

(10) Patent No.: US 10,659,172 B2
(45) Date of Patent: May 19, 2020

(54) CAPSULE ENDOSCOPE TRANSMITTER AND CAPSULE ENDOSCOPE RECEIVER CONFIGURED TO PERFORM HUMAN BODY COMMUNICATION AND HUMAN BODY COMMUNICATION METHOD USING THE SAME

(71) Applicant: ELECTRONICS AND TELECOMMUNICATIONS RESEARCH INSTITUTE, Daejeon (KR)

(72) Inventors: In Gi Lim, Daejeon (KR); Hyung-Il Park, Daejeon (KR); Sung Weon Kang, Daejeon (KR); Tae Wook Kang, Daejeon (KR); Sung Eun Kim, Daejeon (KR); Jung Bum Kim, Daejeon (KR); Mi Jeong Park, Daejeon (KR); Seong Mo Park, Daejeon (KR); Kwang Il Oh, Daejeon (KR); Byounggun Choi, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 244 days.

(21) Appl. No.: 15/616,788

(22) Filed: Jun. 7, 2017

(65) Prior Publication Data
US 2018/0026729 A1 Jan. 25, 2018

(30) Foreign Application Priority Data

Jul. 20, 2016 (KR) .................. 10-2016-0092257
Jan. 31, 2017 (KR) .................. 10-2017-0013994

(51) Int. Cl.
*A61B 1/00* (2006.01)
*A61B 1/04* (2006.01)
(Continued)

(52) U.S. Cl.
CPC ....... *H04B 13/005* (2013.01); *A61B 1/00006* (2013.01); *A61B 1/00009* (2013.01);
(Continued)

(58) Field of Classification Search
CPC ........ H04B 13/005; H04J 3/0608; H04J 3/06; H04J 3/1694; H04J 2013/0096;
(Continued)

(56) References Cited

U.S. PATENT DOCUMENTS 7,124,156 B2 * 10/2006 Yang ................ G06F 7/584
708/252
8,798,049 B2  8/2014 Lim et al.
(Continued)

FOREIGN PATENT DOCUMENTS

KR   10-2005-0067330 A   7/2005
KR   10-2009-0062486 A   6/2009
(Continued)

*Primary Examiner* — Moo Jeong

(57) ABSTRACT

The present disclosure relates to a capsule endoscope transmitter configured to transmit frames including control frames and data frames to a capsule endoscope receiver. The capsule endoscope transmitter includes a preamble generator configured to generate preambles for synchronizing and identifying the control frames used to select a reception electrode pair that receives the frames, and a line sync generator configured to generate a line sync for synchronizing the data frames and identifying a code value of each of the data frames.

16 Claims, 9 Drawing Sheets

(51) Int. Cl.
*H04B 13/00* (2006.01)
*H04J 13/00* (2011.01)
*H04J 13/10* (2011.01)
*H04J 3/06* (2006.01)
*H04J 3/16* (2006.01)
*H04L 5/00* (2006.01)
*H04L 7/04* (2006.01)
*H04N 5/225* (2006.01)

(52) U.S. Cl.
CPC .......... *A61B 1/00016* (2013.01); *A61B 1/041* (2013.01); *H04J 3/06* (2013.01); *H04J 3/0608* (2013.01); *H04J 3/1694* (2013.01); *H04L 7/043* (2013.01); *H04N 5/2256* (2013.01); *A61B 2562/04* (2013.01); *H04L 5/0044* (2013.01); *H04L 5/0053* (2013.01); *H04N 2005/2255* (2013.01)

(58) Field of Classification Search
CPC ....... H04J 13/10; H04J 13/0022; H04L 7/043; H04L 5/0053; H04L 5/0044; A61B 1/00009; A61B 1/041; A61B 1/00016; A61B 1/00006; A61B 2562/04; H04N 5/2256; H04N 2005/2255
See application file for complete search history.

(56) References Cited

U.S. PATENT DOCUMENTS

| | | | |
|---|---|---|---|
| 2007/0147336 A1 | 6/2007 | Lee et al. | |
| 2010/0246643 A1 | 9/2010 | Lim et al. | |
| 2010/0272156 A1 | 10/2010 | Park et al. | |
| 2011/0058615 A1* | 3/2011 | Park ........................ | H04J 13/16 375/259 |
| 2012/0201235 A1* | 8/2012 | Lim ................... | A61B 1/00016 370/349 |
| 2015/0097654 A1* | 4/2015 | Mo .................... | G06K 7/10009 340/10.4 |

FOREIGN PATENT DOCUMENTS

| | | |
|---|---|---|
| KR | 10-2011-00275300 A | 3/2011 |
| KR | 10-1309616 B1 | 9/2013 |
| KR | 10-1580479 B1 | 12/2015 |

* cited by examiner

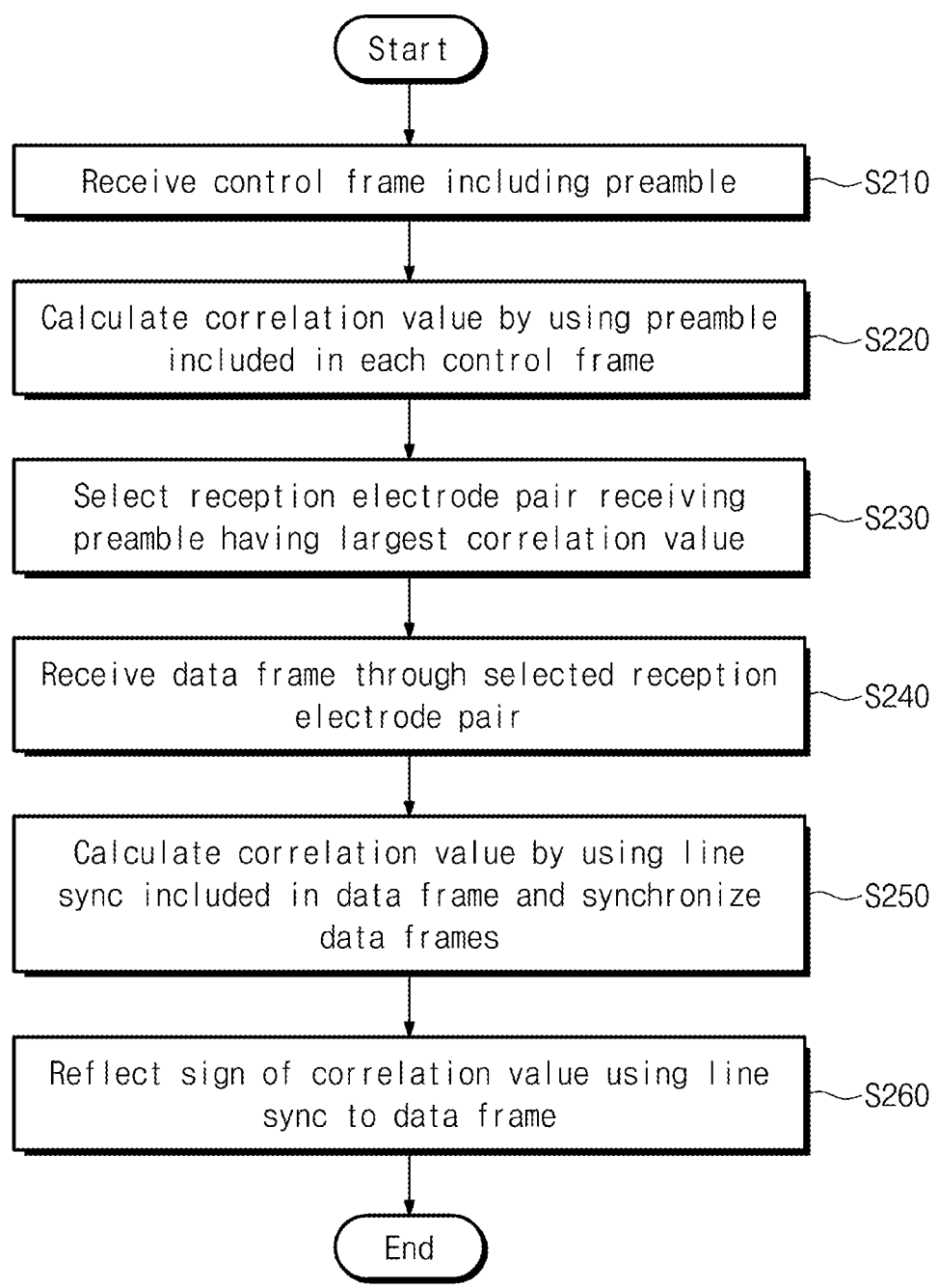

CAPSULE ENDOSCOPE TRANSMITTER AND CAPSULE ENDOSCOPE RECEIVER CONFIGURED TO PERFORM HUMAN BODY COMMUNICATION AND HUMAN BODY COMMUNICATION METHOD USING THE SAME

CROSS-REFERENCE TO RELATED APPLICATIONS

This U.S. non-provisional patent application claims priority under 35 U.S.C. § 119 of Korean Patent Application Nos. 10-2016-0092257, filed on Jul. 20, 2016, and 10-2017-0013994, filed on Jan. 31, 2017, the entire contents of which are hereby incorporated by reference.

BACKGROUND

The present disclosure herein relates to a capsule endoscope, and more particularly, to a preamble generator and a line sync generator of a capsule endoscope transmitter.

The present disclosure herein relates to a capsule endoscope, and more particularly, to a line sync processor of a capsule endoscope receiver.

The present disclosure herein relates to a capsule endoscope, and more particularly, to a human body communication method using a capsule endoscope transmitter and a capsule endoscope receiver.

A capsule endoscope captures the internal organs of a human body and delivers the captured image to the outside. For this purpose, there is a demand for a transmission device for transmitting a captured image to the outside of a human body and a reception device for receiving the transmitted data. As a method of performing such communication, there are a method using a radio frequency (RF) and a method using human body communication.

When an image captured by a capsule endoscope is transmitted to the outside of a human body using human body communication, it is very important to find a position (e.g., a stomach, a back, a side, etc.) of a human body through which the captured image is efficiently transmitted. That is, it is very important to select a pair of optimal reception electrodes among a plurality of reception electrodes for receiving a captured image. Therefore, control frames generated by a capsule endoscope may be transmitted to the outside of a human body before a captured image is transmitted.

On the other hand, the capsule endoscope may be constantly moved inside the human body, and this may affect a data frame including the captured image. Therefore, it is very important to reflect the influence of the constantly moving capsule endoscope to the data frame.

SUMMARY

The present disclosure provides a preamble used for selecting an optimal reception electrode pair that efficiently delivers a data frame to the outside of a human body when human body communication is performed using a capsule endoscope.

The present disclosure also provides a line sync used for efficiently evaluating a code value of changing data when human body communication is performed using a capsule endoscope.

An embodiment of the inventive concept provides a capsule endoscope transmitter configured to transmit frames including control frames and data frames to a capsule endoscope receiver, the capture endoscope transmitter includes: a preamble generator configured to generate preambles for synchronizing and identifying the control frames used to select a reception electrode pair that receives the frames; and a line sync generator configured to generate a line sync for synchronizing the data frames and identifying a code value of each of the data frames.

In an embodiment of the inventive concept, a capsule endoscope receiver configured to receive a data frame includes a line sync and data, including a line sync processor configured to calculate a correlation value by using the line sync including bits repeated at least twice, synchronize the data frame by using the correlation value, and reflect an XOR operation result for the data and a sign of the correlation value to the data frame.

In an embodiment of the inventive concept, a method of performing human body communication by using a capsule endoscope transmitter and a capsule endoscope receiver includes: generating preambles for synchronizing a plurality of control frames and identifying the plurality of control frames; and generating a line sync for synchronizing a plurality of data frames transmitted subsequent to the plurality of control frames and identifying a sign value of each of the plurality of data frames.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIG. 11 is a flowchart illustrating an operation method of a capsule endoscope receiver according to an embodiment of the inventive concept.

DETAILED DESCRIPTION

In the following, embodiments of the inventive concept will be described in detail so that those skilled in the art easily carry out the inventive concept.

Figure 1:
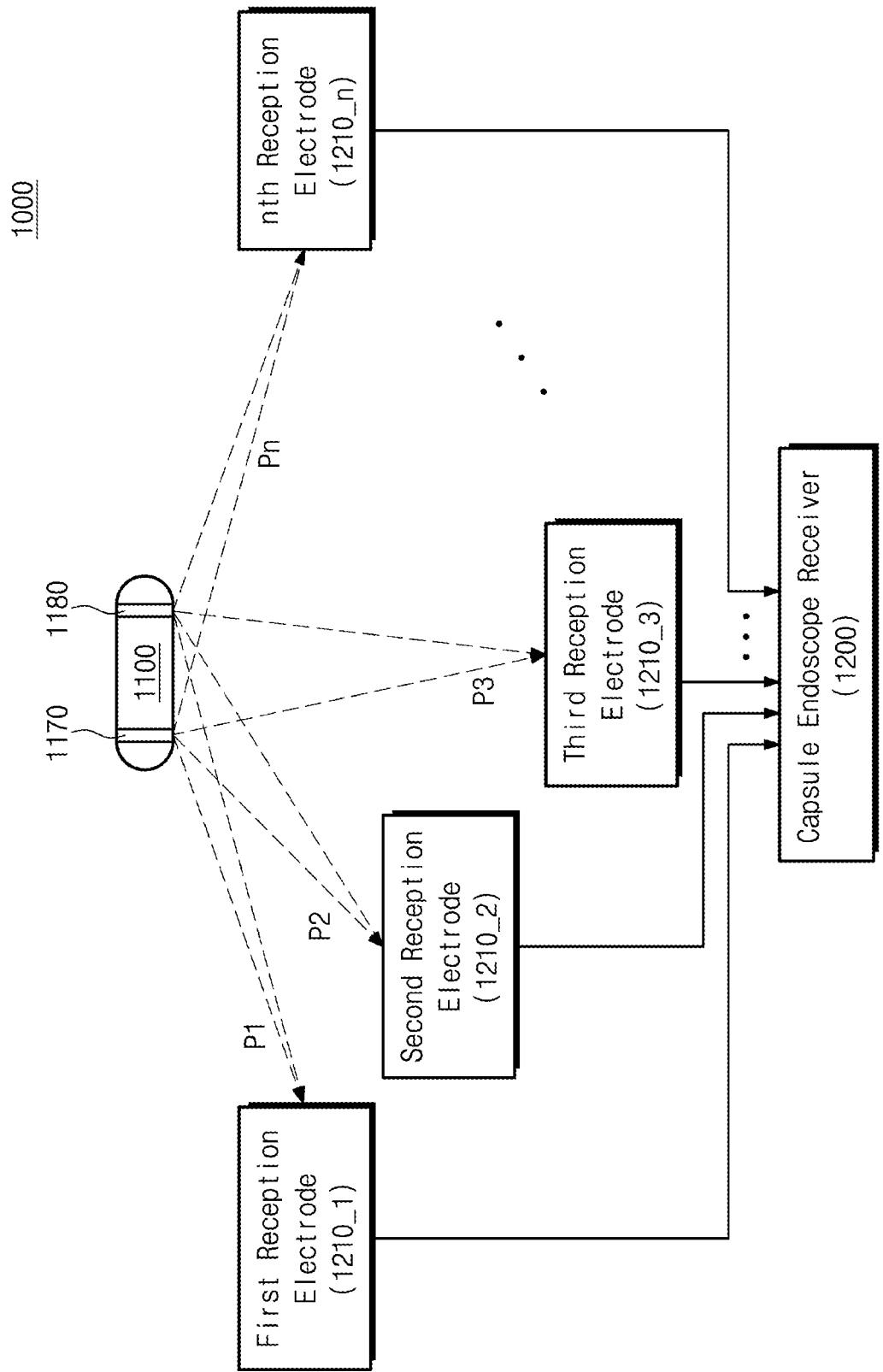
FIG. 1 is a view illustrating a human body communication system according to an embodiment of the inventive concept.

FIG. 1 is a view illustrating a human body communication system 1000 according to an embodiment of the inventive concept. The human body communication system 1000 may include a capsule endoscope 1100 and a capsule endoscope receiver 1200. Although a plurality of reception electrodes 1210_1 to 1210_n are shown separately from the capsule endoscope receiver 1200, they may be considered to be components of the capsule endoscope receiver 1200.

The capsule endoscope 1100 may be configured to capture the internal organs after being taken by a user. In order to perform such an operation, the capsule endoscope 1100 may include a light emitting element such as an LED, an image sensor for capturing an image, an image data generator for processing a captured image to be suitable for transmission, a transmitter for transmitting a signal processed by the image data generator to the outside of a human body, and a battery for driving the capsule endoscope 1100.

The capsule endoscope 1100 may include a transmission electrode 1170 and a ground electrode 1180 for realizing human body communication. For example, control frames indicating the preparation of transmission may be transmitted to the transmission electrode 1170 before the transmitting of a captured image. Then, the captured image may be processed into data frames to be suitable for transmission and transmitted to the transmission electrode 1170. At this time, the current generated due to the potential difference between the transmission electrode 1170 and the ground electrode 1180 may flow to the outside of a human body through the human body.

On the other hand, when the capsule endoscope 1100 is taken by a user, the capsule endoscope 1100 continuously moves inside the organ. Accordingly, the reception sensitivity of a signal transmitted by the capsule endoscope 1100 may differ depending on the position and/or direction of the capsule endoscope 1100, the position of a sensor for receiving a signal, and the like. If a signal transmitted from the capsule endoscope 1100 and a signal received by the capsule endoscope receiver 1200 are the same, this means that there is no signal distortion in the transmission and reception processes. Hereinafter, the degree of correlation or the value of correlation is defined to be larger as the patterns of the signal transmitted from the capsule endoscope 1100 and the signal received by the capsule endoscope receiver 1200 are matched to each other. Accordingly, in order to completely transmit the image taken by the long-term capsule endoscope 1100 through the human body communication to the outside, a channel having a high degree of correlation (i.e., a pair of receiving electrodes on which a signal having the highest correlation value is received) It is necessary to transmit a data frame.

The capsule endoscope 1100 may generate preambles before transmitting the data frame to the outside of the capsule endoscope 1100. The preambles may constitute control frames, and may include various information required for frame synchronization, frame identification, and/or the like. The preambles may be used for selecting one pair of reception electrodes that receive the largest correlation value among the plurality of reception electrodes 1210_1 to 1210_n. The structure of the frame according to an embodiment of the inventive concept will be described in more detail with reference to FIG. 3.

A preamble generator (not shown) included in the capsule endoscope 1100 may generate a plurality of preambles including a short preamble and a long preamble. For example, each preamble may be used to determine the correlation value of a signal, and may include information for distinguishing a preamble from other preambles. For example, each of the preambles may be transmitted to one pair of selectable reception electrodes among the plurality of reception electrodes 1210_1 to 1210_n.

The capsule endoscope receiver 1200 may include a plurality of reception electrodes 1210_1 to 1210_n for receiving control frames and data frames. For example, each of the plurality of reception electrodes 1210_1 to 1210_n may be attached to a human body (e.g., a stomach, a back, a side, etc.). For example, the capsule endoscope receiver 1200 may receive control frames and data frames by detecting the phase difference of the current received through two arbitrarily selected reception electrodes among the plurality of reception electrodes 1210_1 to 1210_n. For example, the capsule endoscope receiver 1200 may receive a data frame through one pair of reception electrodes that receive a preamble having the largest correlation value among the plurality of reception electrodes 1210_1 to 1210_n.

According to the inventive concept for generating a preamble composed of a short preamble and a long preamble before transmitting a data frame, a frame may be synchronized using a preamble having a relatively simple structure. In addition, it is possible to maintain a preamble having a sufficient length required for calculating the correlation value. Therefore, since the structure of the frame is simplified, the efficiency of human body communication may be improved.

Figure 2:
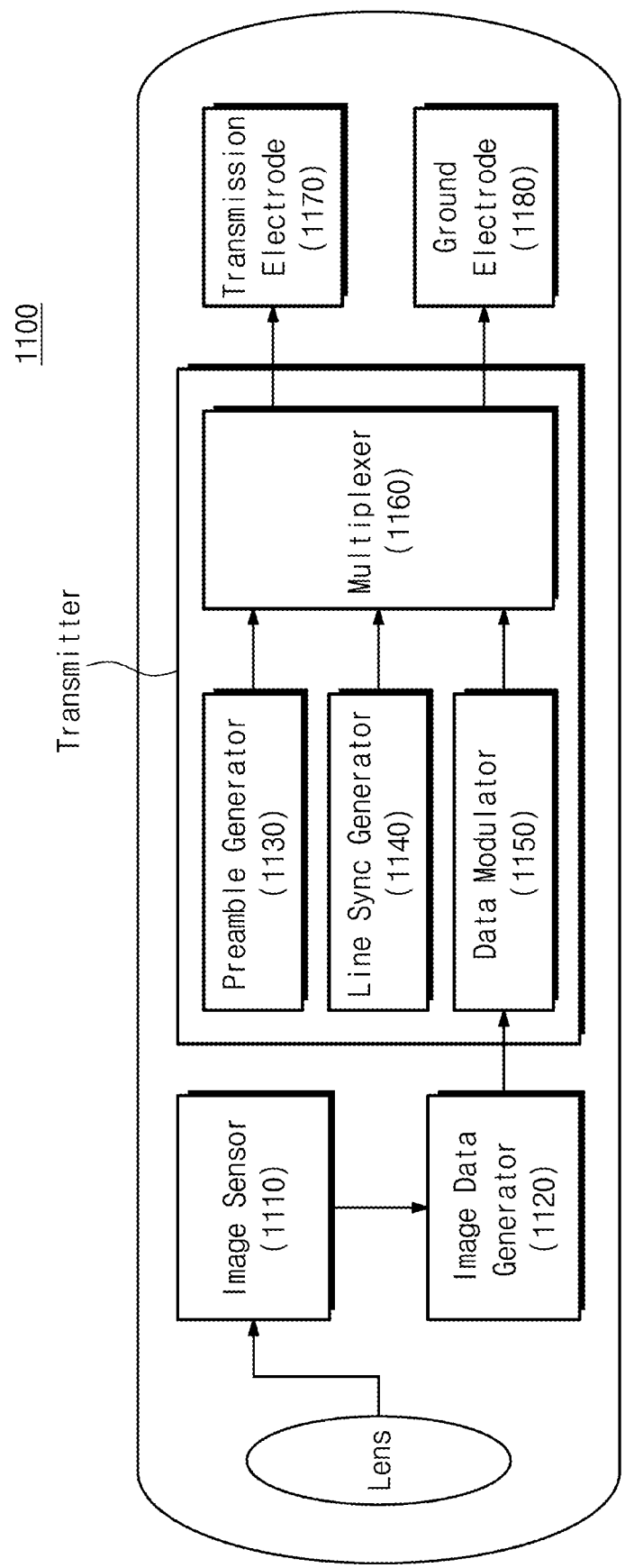
FIG. 2 is a block diagram illustrating a configuration of a capsule endoscope according to an embodiment of the inventive concept.

FIG. 2 is a block diagram illustrating a configuration of a capsule endoscope 1100 according to an embodiment of the inventive concept. The capsule endoscope 1100 may include a lens, an image sensor 1110, an image data generator 1120, a preamble generator 1130, a line sync generator 1140, a data modulator 1150, a multiplexer 1160, a transmission electrode 1170, and a ground electrode 1180. The preamble generator 1130, the line sync generator 1140, the data modulator 1150, and the multiplexer 1160 may constitute a transmitter of the capsule endoscope 1100.

The image sensor 1110 may process an internal organ image taken by the lens to generate digitized image data. The image sensor 1110 may be a Charge Coupled Device (CCD) or a Complementary Metal-Oxide Semiconductor Image Sensor (CMOS), but is not limited thereto. For example, the image sensor 1110 may include an active pixel sensor array for converting optical signals to electrical signals, a correlated dual sampler that for sampling and holding signals from the active pixel sensor array, an analog to digital converter for converting signals from the correlated dual sampler.

The image data generator 1120 receives the image data generated by the image sensor to provide the image data that the data modulator 1150 needs at a desired time, and adds image information to the image data to generate an image frame. The plurality of image frames may constitute a data frame.

The preamble generator 1130 may generate preambles that notify the transmission of a data frame before the data frame is transmitted. For example, the preamble generator 1130 may generate short preambles and long preambles. For example, each preamble may include a plurality of short preambles (or at least one short preamble) and one long preamble. The preamble may include data necessary for synchronizing a plurality of preambles and a control frame composed of a plurality of switching times, and may include data necessary for calculating a correlation value. Then, the preamble may include data indicating whether the frame received by the capsule endoscope receiver 1200 (see FIG. 1) is a control frame or a data frame. For example, the preamble generator 1130 may include a pseudo-random number generator and a Manchester encoder.

The line sync generator 1140 may generate information required for synchronizing the data frames transmitted to the capsule endoscope receiver 1200. For example, the line syncs generated by the line sync generator 1140 may be added to the front ends of the data frame, respectively. For example, the line sync generator 1140 may include a pseudo-random number generator, a Manchester encoder, and a repeater.

The Data modulator 1150 may receive and modulate an image frame from image data generator 1120. In modulating an image frame, various types of modulation may be used. For example, the data modulator 1150 may modulate an image frame by using Frequency Selective Digital Transmission (FSDT) using a frequency-selective spreading code.

The multiplexer 1160 may receive the short preambles and the long preamble generated by the preamble generator 1130 to generate preambles. For example, the multiplexer 1160 may generate a plurality of preambles by combining a plurality of short preambles (or at least one short preamble) and a long preamble. The preambles may be respectively transmitted to one pair of selectable reception electrodes among the plurality of reception electrodes 1210_1 to 1210_n (see FIG. 1). For example, the long preambles included in each of the preambles may have different bit values. That is, by analyzing the long preamble included in each preamble, it is possible to identify what number the preamble is.

The multiplexer 1160 may receive the line sync generated by the line sync generator 1140 and the image frame modulated by the data modulator to generate a data frame. For example, a multiplexer may add a line sync to the front of an image frame to generate a data frame.

The multiplexer 1160 may transmit preambles and data frames to the transmission electrode 1170. A current may be generated by a potential difference between a signal delivered to the outside through the transmission electrode 1160 and the ground electrode 1180, and the generated current may be delivered to the plurality of external reception electrodes 1210_1 to 1210_n (see FIG. 1) through a human body.

Although not shown in the drawing, the transmitter of the capsule endoscope 1100 may further include a component for adding a header and a cyclic redundancy check (CRC) to the data frame. For example, a header may be added to the front end of an image frame and may be used to identify the type of a frame. The CRC may be added to the back end of the image frame and may be used to detect an error in the data frame upon reception by the capsule endoscope receiver 1200 (see FIG. 1).

Figure 3:
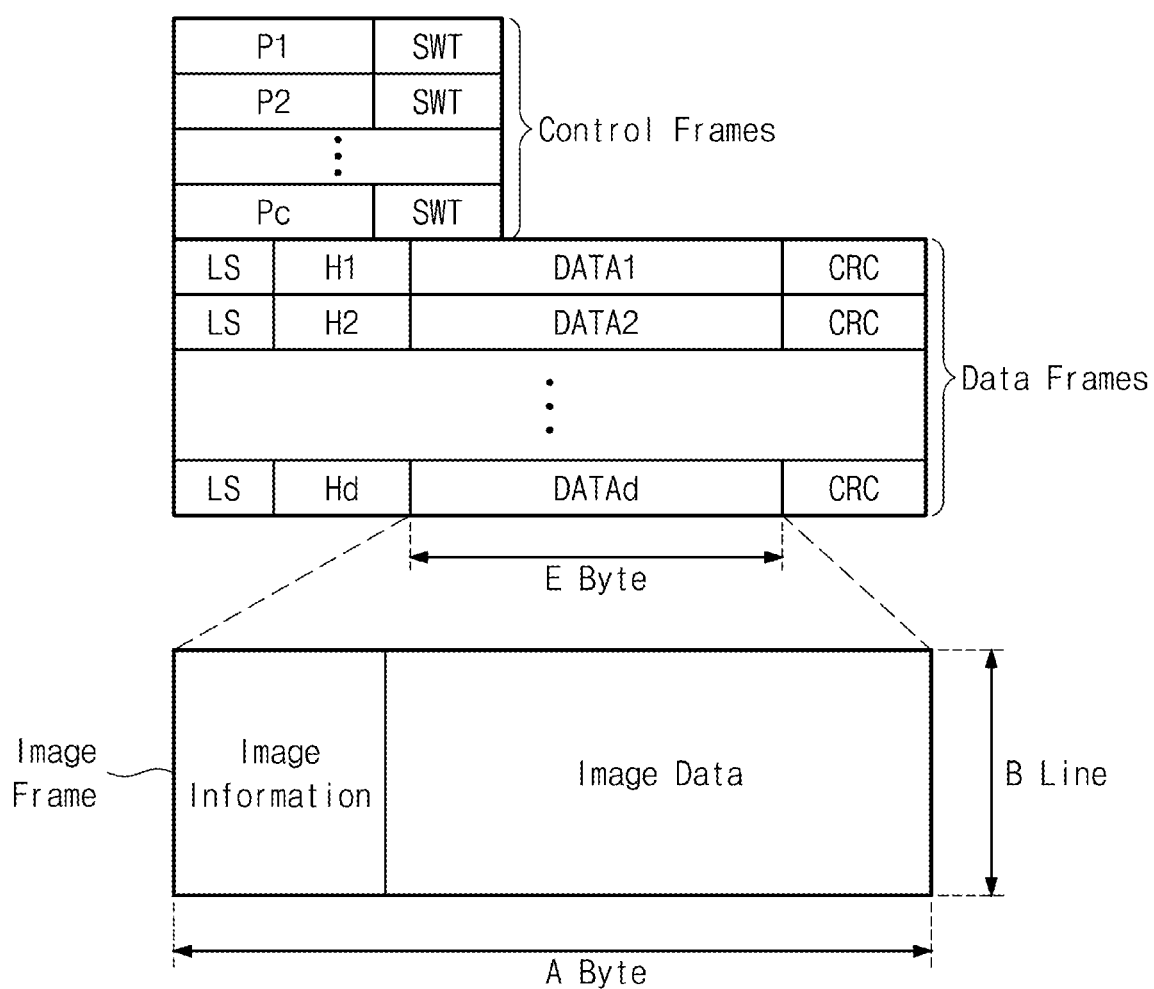
FIG. 3 is a view illustrating a configuration of frames according to an embodiment of the inventive concept.

FIG. 3 is a view illustrating a configuration of frames according to an embodiment of the inventive concept. In performing human body communication according to an embodiment of the inventive concept, control preambles and data frames may be transmitted. To help understanding of the description, FIG. 1 and FIG. 2 will be described together.

In performing human body communication, control frames may be transmitted from the capsule endoscope 1100 to the capsule endoscope receiver 1200 first. For example, the control frames may be transmitted to the plurality of receiving electrodes 1210_1 to 1210_n, respectively. Each of the plurality of control frames may include one of a plurality of preambles P1 to Pc and a switching time (SWT). Exemplarily, it is described that the control frames include c control frames.

The preambles P1 to Pc may be used to synchronize control frames and calculate the correlation value of the preamble. In addition, the preambles P1 to Pc may include information notifying whether the frame received by the capsule endoscope receiver 1200 is a control frame or a data frame.

The switching time SWT may be a time required to select one pair of selectable reception electrodes among the plurality of receiving electrodes 1210_1 to 1210_n. For example, dummy patterns may be transmitted to the capsule endoscope receiver 1200 during the switching time SWT.

The number of control frames (i.e., c) may be determined by the number (i.e., n) of the plurality of reception electrodes 1210_1 to 1210_n. For example, the number of cases in which two different reception electrodes among the n reception electrodes are selected may be expressed by the following Equation 1.

$$_nC_2 = \frac{n!}{(n-2)! * 2!} \qquad \text{[Equation 1]}$$

Each of the c control frames may be received by the capsule endoscope receiver 1200 through one pair of selectable reception electrodes among the plurality of reception electrodes 1210_1 to 1210_n. A correlation value for each of the received c preambles may be compared and one pair of reception electrodes that receive a preamble having the largest correlation value may be selected as a channel for receiving a data frame.

If the electrode pair that receives the preamble having the largest correlation value is selected according to the transmission of the control frame, the data frame may be transmitted to the selected reception electrode pair. The data frame may be a frame for transmitting image data corresponding to the image captured by the capsule endoscope 1100. For example, each of the data frames may include a line sync LS, any one of the headers H1 to Hd, any one of the data DATA1 to DATAd, and a CRC. Here, the data DATA1 to DATAd may correspond to the image frames, respectively.

The line sync LS may be used to synchronize data frames. For example, a correlation value may be calculated using the bit values included in the line sync LS, and the data frames may be synchronized using the calculated correlation value.

The line sync LS may be used to determine the sign of the data frame. For example, while the capsule endoscope 1100 is moving within an internal organ, the sign of the data frame may vary depending on the direction or angle of the transmission electrode 1170 and the reception electrode of the capsule endoscope 1100. Therefore, it is necessary to determine the sign of the data frame changing in real time. The sign of a calculated correlation value used in the above synchronization of the data frame may be stored and a logic operation (e.g., XOR) may be performed on the received header, data, and a CRC following the line sync LS, so that the sign value may be reflected for each data frame.

Each of the headers H1 to Hd may include information on a data frame such as a frame delimiter (or identifier) and a line number for identifying data frames. However, the information included in the headers is not limited thereto, and may include various information on a data frame other than image data or a CRC.

Each of the data DATA1 to DATAd may include information of an image frame. Exemplarily, it is shown that data consists of E bytes. The number d of data frames, the length E bytes of data, and the A bytes and B lines of an image frame have the relationship shown in Equation 2 below.

$$A \text{ bytes} \times B \text{ lines} = E \text{ bytes} \times \text{NUMBER OF DATA FRAMES } d \quad \text{[Equation 2]}$$

To help understanding of the description, it is assumed that the image data read by the image sensor 1110 is composed of 480 bytes×480 lines and the image information added to the image data is composed of 480 bytes×2 lines. In this case, the data of each data frame may be composed of 480 bytes×482 lines.

According to such a frame structure, each of the control frames may be transmitted to one pair of selectable reception electrodes among a plurality of reception electrodes, and a data frame may be transmitted to one pair of reception electrodes that receive a preamble having the largest correlation value. Unlike the general case, the preamble does not include a header, and a preamble is identified by using a long preamble included in the preamble. Then, since the data frames are synchronized and also the code value of each frame is identified using the line sync included in the data frame, the frame structure may be simplified.

Figure 4:
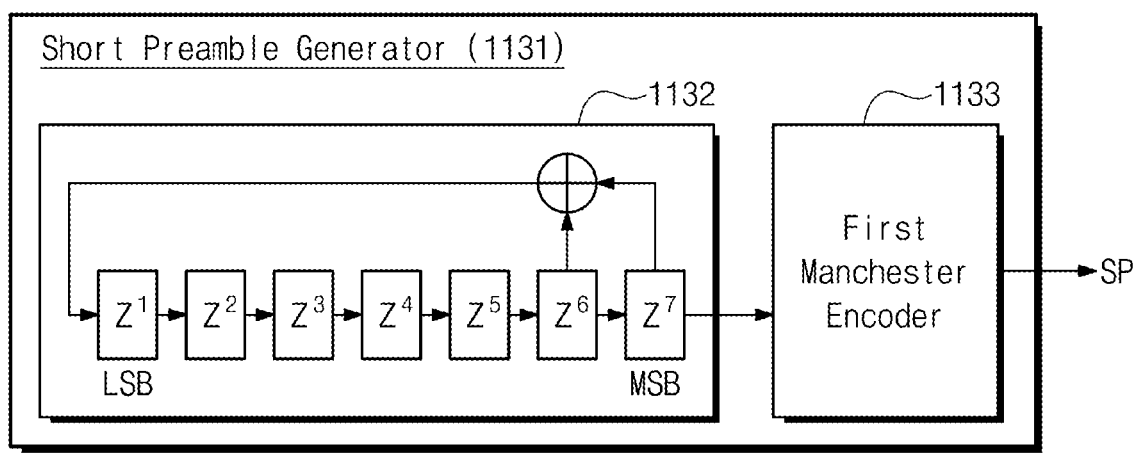
FIGS. 4 and 5 are block diagrams illustrating an exemplary configuration of a preamble generator shown in FIG. 2.
Figure 5:
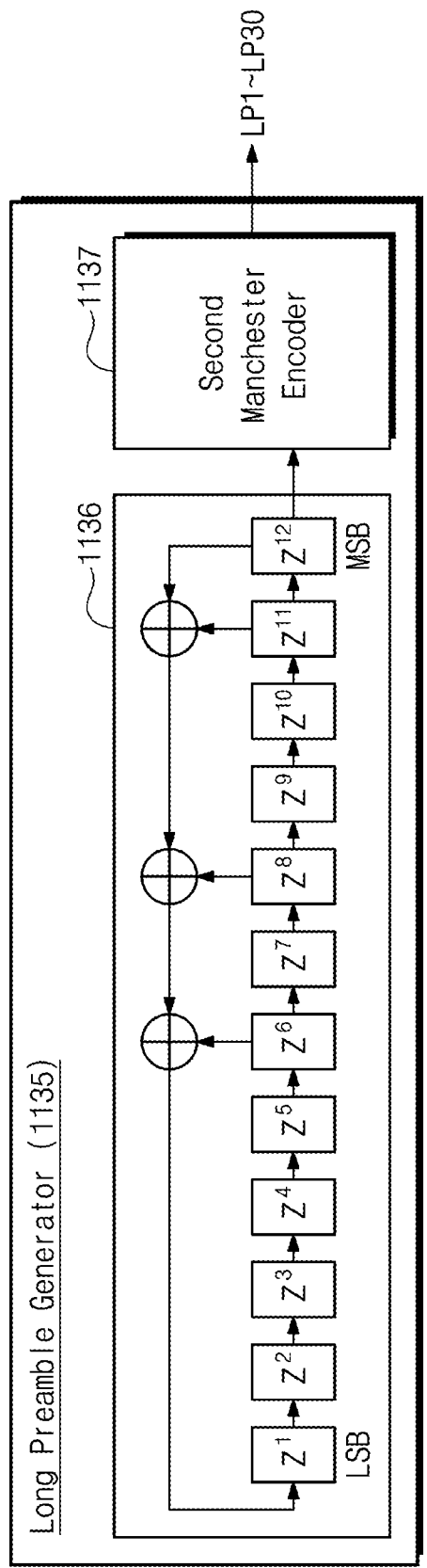

FIGS. 4 and 5 are block diagrams illustrating an exemplary configuration of the preamble generator 1130 shown in FIG. 2. Referring to FIGS. 4 and 5, the preamble generator 1130 may include a short preamble generator 1131 and a long preamble generator 1135.

Referring to FIG. 4, the short preamble generator 1131 may include a first pseudo-random number generator 1132 and a first Manchester encoder 1133.

The first pseudo-random number generator 1132 may generate a 128-bit pseudo-random number. For example, the generator polynomial of the first pseudo-random number generator 1132 may be $P(z)=z^7+z^6+1$, and the initial value may be '1000000'. However, such an initial value is exemplary and the initial value may be different from that. The first Manchester encoder 1133 may perform encoding to prevent a particular bit from being repeatedly outputted. For example, the first Manchester encoder 1133 may encode bit '0' to bits '01' and bit '1' to bits '10'. According to a result of encoding by the first Manchester encoder 1131, 256 bit data may be generated and provided as bit values constituting the shot preamble SP.

Referring to FIG. 5, the long preamble generator 1135 may include a second pseudo-random number generator 1136 and a second Manchester encoder 1137.

The second pseudo-random number generator 1136 may generate a 4096-bit pseudo-random number. For example, the generator polynomial of the second pseudo-random number generator 1136 may be $P(z)=z^{12}+z^{11}+z^8+z^6+1$, and the initial value may be '100000000000'. However, such an initial value is exemplary and the initial value may be different from that.

The second Manchester encoder 1137 may perform encoding to prevent a particular bit from being repeatedly outputted. For example, the second Manchester encoder 1137 may encode bit '0' to bits '01' and bit '1' to bits '10'. According to a result of encoding by the second Manchester encoder 1137, 8192 bit data may be generated and provided as bit values constituting long preambles LP1 to LP30. For example, when control frames are composed of 30 long preambles and each long preamble is composed of 256 bit data, only 7680 bits among 8192 bit data may be used.

Exemplarily, the first pseudo-random number generator 1131 and the second pseudo-random number generator 1136 are shown as being 7-bit and 12-bit pseudo-random number generators, respectively, but are not limited thereto. That is, the data generated by the first pseudo-random number generator 1131 may have a different number of bits than the 128 bits, and the data generated by the second pseudo-random number generator 1136 may have a different number of bits than the 4096 bits.

Then, although it is shown exemplarily that Manchester encoders are used in the first pseudo-random number generator 1131 and the second pseudo-random number generator 1136, the inventive concept is not limited thereto. For example, various types of encoders (e.g., Walsh encoders, etc.) may be used to generate random numbers by preventing bits from being repeatedly outputted.

Figure 6:
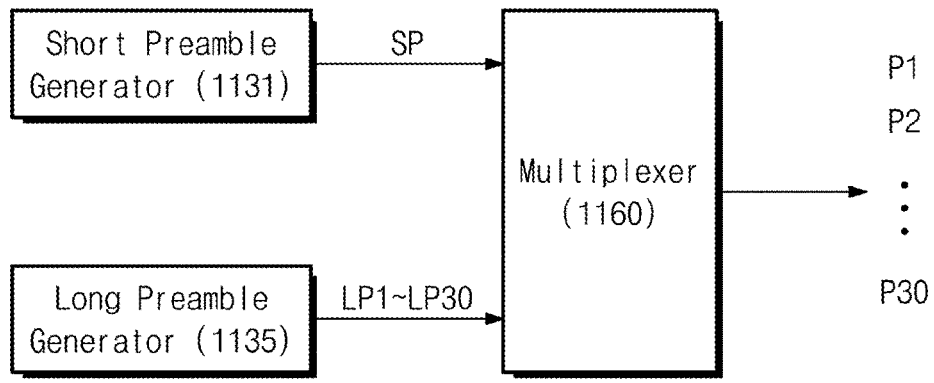
FIG. 6 is a block diagram illustrating an operation of generating a plurality of preambles using a short preamble and long preambles.

FIG. 6 is a block diagram illustrating an exemplary operation of generating a plurality of preambles P1 to P30 using a short preamble SP and long preambles LP1 to LP30. To help understanding of the description, FIG. 1 and FIG. 6 will be described together.

For example, in the case of receiving preambles using eight reception electrodes of the capsule endoscope receiver 1200 according to Equation 1 described above, the number of combinable pairs of reception electrodes is 28 in total. Therefore, a total of 28 preambles may be transmitted to a pair of combinable electrodes. However, according to an embodiment, additional (or extra) preambles may be further generated. For example, it is assumed that 30 control frames are received by the capsule endoscope receiver 1200 through eight reception electrodes.

The short preamble generator 1131 may repeatedly generate a short preamble SP having a specific number of bits using a pseudo-random number generator and a Manchester encoder. Then, the long preamble generator 1136 may generate the long preambles LP1 to LP30 having longer bits than the short preamble SP. For example, the short preamble SP and each long preamble may be composed of 256 bit data.

The multiplexer 1160 may generate a plurality of preambles by combining the short preamble SP and the long preambles LP1 to LP30. For example, the multiplexer 1160 may generate one preamble (e.g., P1) using three short preambles SP and one long preamble (e.g., LP1). For example, one preamble may be composed of 1024 bit data.

For example, the configuration of such a preamble may be a value set considering a sufficient number of bits needed to synchronize the frames. Then, the configuration of the preamble may be a value set considering a sufficient number of bits to calculate a correlation value for selecting one pair of reception electrodes among a plurality of reception electrodes 1210_1 to 1210_n (see FIG. 1).

Figure 7:
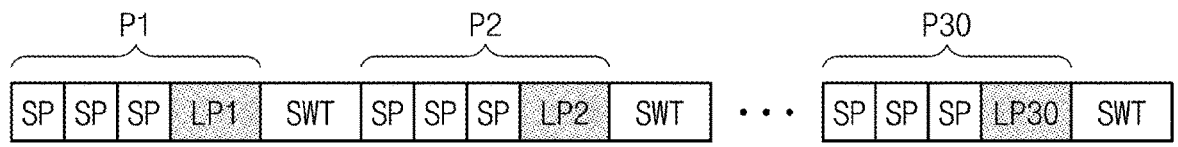
FIG. 7 is a view illustrating a configuration of control frames outputted from a multiplexer shown in FIG. 6.

FIG. 7 is a view illustrating a configuration of control frames outputted from the multiplexer 1160 shown in FIG. 6.

Each of the plurality of control frames may be configured with one of the preambles P1 to P30 and the switching time SWT. For example, the control frame may be transmitted 30 times. Each control frame is to be received by the capsule endoscope receiver 1200 through one or more combinable reception electrodes.

Short preambles and long preambles included in each control frame may be used for synchronization of frames. The long preamble included in each control frame may include information for checking what number the received control frame is. Then, a long preamble included in each control frame may include information for checking whether the received frame is a control frame or a data frame. Then, information related to the image frame, such as the number of the image frame and the image exposure time, may be included in the beginning part of the data frame and transmitted. For example, information related to such an image frame may be included in the first two lines of the data frame among the data frames shown in FIG. 3 and transmitted.

According to such a preamble structure, since the header function of a header added to a control frame is generally included in a preamble, the configuration of the control frame may be simplified. That is, by analyzing the generated preamble according to an embodiment of the inventive concept, it may be possible to determine whether or not the received frame is a control frame, and also it may be possible to determine what number the received control frame is.

Figure 8:
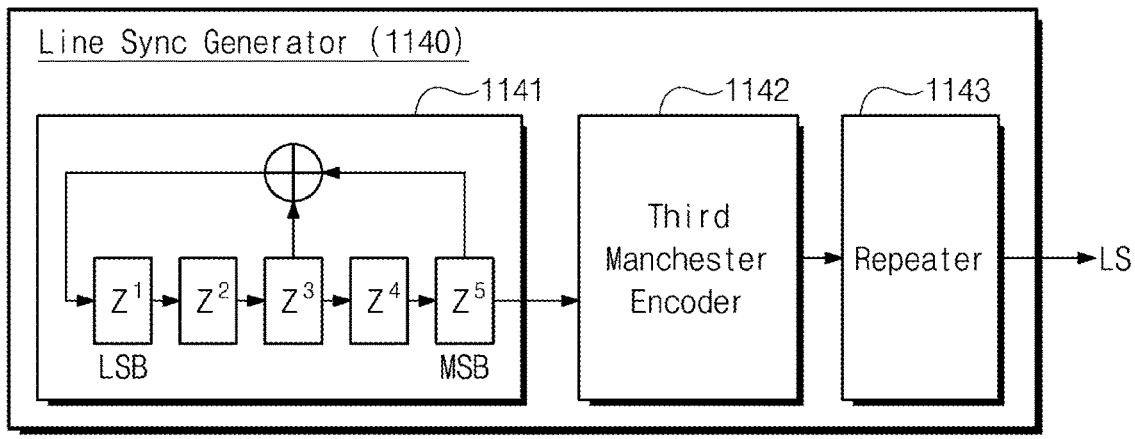
FIG. 8 is a block diagram illustrating an exemplary configuration of a line sync generator shown in FIG. 2.

FIG. 8 is a block diagram illustrating an exemplary configuration of the line sync generator 1140 shown in FIG. 2. To help understanding of the description, FIG. 2 and FIG. 3 will be described together.

The line sync generator 1140 may include a third pseudo-random number generator 1141, a third Manchester encoder 1142, and a repeater 1143.

The third pseudo-random number generator 1141 may generate a 32-bit pseudo-random number. For example, the generator polynomial of the third pseudo-random number generator 1141 may be $P(z)=z^5+z^3+1$, and the initial value may be '10000'. However, such an initial value is exemplary and the initial value may be different from that.

The third Manchester encoder 1142 may perform encoding to prevent a particular bit from being continuously outputted. For example, the third Manchester encoder 1142 may encode bit '0' to bits '01' and bit '1' to bits '10'. As a result of the encoding by the third Manchester encoder 1142, 64 bit data may be generated.

The repeater 1143 may generate the data of bits longer than 64 bits by repeating a plurality of times the bit value generated according to a result of encoding by the third Manchester encoder 1142. For example, the repeater 1143 may repeat the output bit of the third Manchester encoder twice to generate 128 bit data. The output of the repeater 1143 may constitute the line sync LS.

Although it is shown exemplarily that the third pseudo-random number generator 1141 is a 5-bit pseudo-random number generator, the inventive concept is not limited thereto. That is, the data generated by the third pseudo-random number generator 1141 may have a different number of bits than the 32 bits. Although it is shown exemplarily that a Manchester encode is used in the third pseudo-random number generator 1142, the inventive concept is not limited thereto. For example, various types of encoders may be used to generate random numbers by preventing bits from being outputted sequentially. For example, the number of repetitions by the repeater 1143 is not limited to two. Alternatively, the repeater 1143 may not be provided according to an embodiment, or the number of repetitions by the repeater 1143 may be one.

Depending on the configuration of the line sync LS generated according to an embodiment of the inventive concept, a change in the sign value of the data frame generated when the capsule endoscope 1100 moves within the organ may be identified. In addition, a logic operation (e.g., XOR) may be performed on the received header, data, and a CRC following the line sync LS, so that the sign value may be reflected for each data frame.

Figure 9:
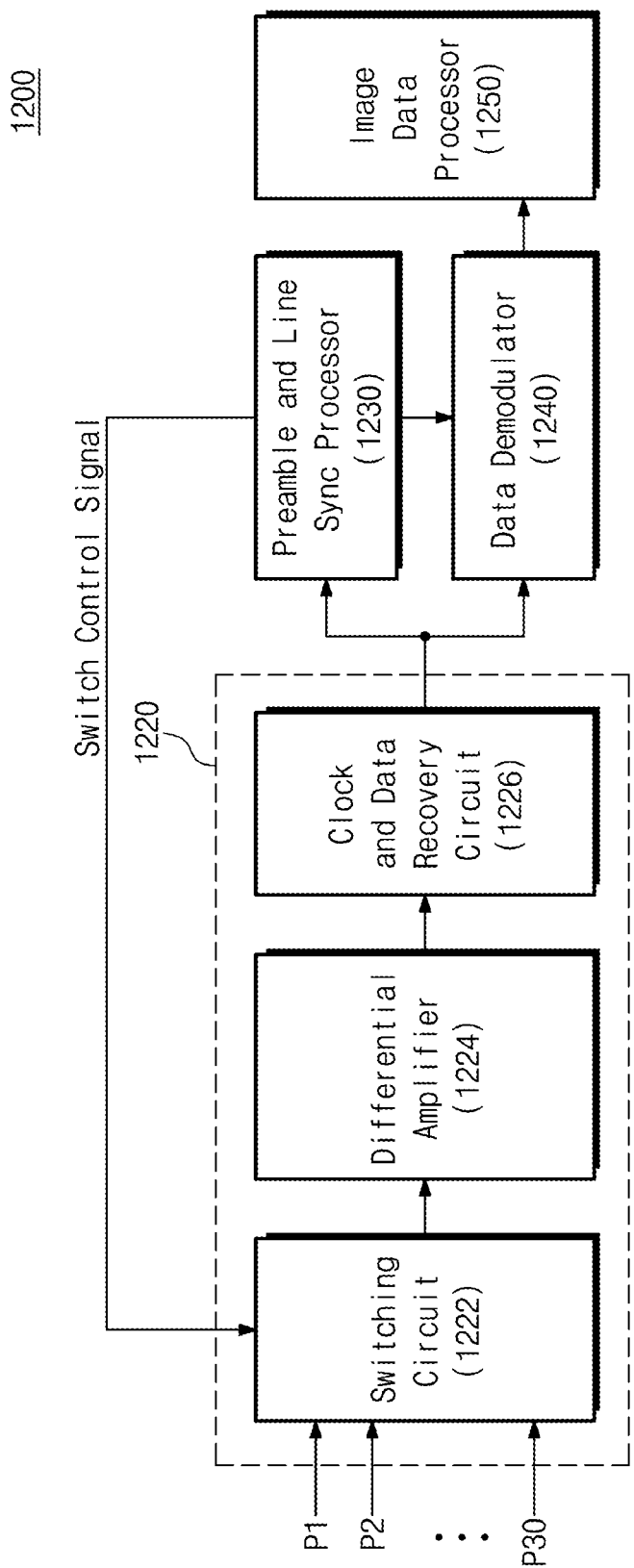
FIG. 9 is a block diagram illustrating an exemplary configuration of a capsule endoscope receiver shown in FIG. 1.

FIG. 9 is a block diagram illustrating an exemplary configuration of the capsule endoscope receiver 1200 shown in FIG. 1. The capsule endoscope receiver 1200 may include an analog reception unit 1220 (or analog front end (AFE)), a preamble and line sync processor 1230, a data demodulator 1240, and an image data processor 1250.

Although the plurality of reception electrodes 1210_1 to 1210_n shown in FIG. 1 are not shown in the drawing, it will be understood that the capsule endoscope receiver 1200 further includes the plurality of reception electrodes 1210_1 to 1210_n shown in FIG. 1. Exemplarily, the plurality of reception electrodes 1210_1 to 1210_n are eight, and 28 reception electrode pairs and two spare reception electrode pairs, which could be selected from eight reception electrodes, are combined to form a total of 30 preambles P1 to P30.

The analog reception unit 1220 may perform a preprocessing on the frame received from the capsule endoscope 1100. As an example of the preprocessing process, there may be switching electrodes to select a reception electrode pair, amplifying a signal received through the selected reception electrode pair, and recovering a clock and data from the amplified signal. In order to perform such an operation, the analog reception unit 1220 may include a switching circuit 1222, a differential amplifier 1224, and a clock and data recovery circuit 1226.

The switching circuit 1222 may select a reception electrode pair that receives a preamble having the largest correlation value. For example, in order to select a reception electrode pair having the largest correlation value, a correlation value should be calculated for the preambles received through all of the combinable reception electrode pairs. Accordingly, the switching circuit 1222 may perform a switching operation so that a correlation value is calculated for each of the preambles P1 to P30.

When the correlation value is calculated for each of the preambles P1 to P30 by the preamble and line sync processor 1230, a reception electrode pair that receives a preamble having the largest correlation value may be selected under the control of the switch control signal. Thereafter, the data frame will be received through the selected reception electrode pair.

The differential amplifier 1224 may amplify the preamble received through the selected reception electrode pair. For example, a signal received through one of the selected reception electrode pair may be transmitted to the first input terminal of the differential amplifier 1224, and a signal received through the other one of the selected reception electrode pair may be transmitted to the second input terminal of the differential amplifier 1224. The signal amplified by the differential amplifier 1224 may be transmitted to the clock and data recovery circuit 1226. [

The clock and data recovery circuit 1226 may recover the clock and data from the amplified signal.

The preamble and line-sync processor 1230 may calculate the correlation value of the preamble received through the combinable reception electrode pair. The preamble and line sync processor 1230 may generate a switch control signal to receive a data frame through the reception electrode pair that receives a preamble having the largest correlation value. Under the control of the switch control signal, the switching circuit may perform a switching operation to select the reception electrode pair that receives a preamble having the largest correlation value. Although it is shown in the drawing that a preamble and a line sync are processed by one functional block, a function of processing the preamble and a function of processing the line sync may be implemented by different functional blocks or circuits, respectively.

The preamble and line sync processor 1230 may synchronize the data frame using the line sync LS received through the selected reception electrode pair. The preamble and line sync processor 1230 may identify and store the sign of the previously calculated correlation value. The preamble and line sync processor 1230 may perform a logical operation (e.g., XOR operation) on the received header, data, and CRC and the stored code value following the line sync LS. The preamble and line sync processor 1230 may reflect the operation result to the sign value of the received data frame.

The data demodulator 1240 may perform demodulation using the data frame recovered by the clock and data recovery circuit 1226 and the code value calculated by the preamble and line sync processor 1230. The data demodulator 1240 may deliver the demodulation result to the image data processor 1250.

The image data processor 1250 may process the demodulated data into data suitable for presentation to the user. For example, the data processed by the image data processor 1250 may be provided to a user through a display device or the like.

Figure 10:
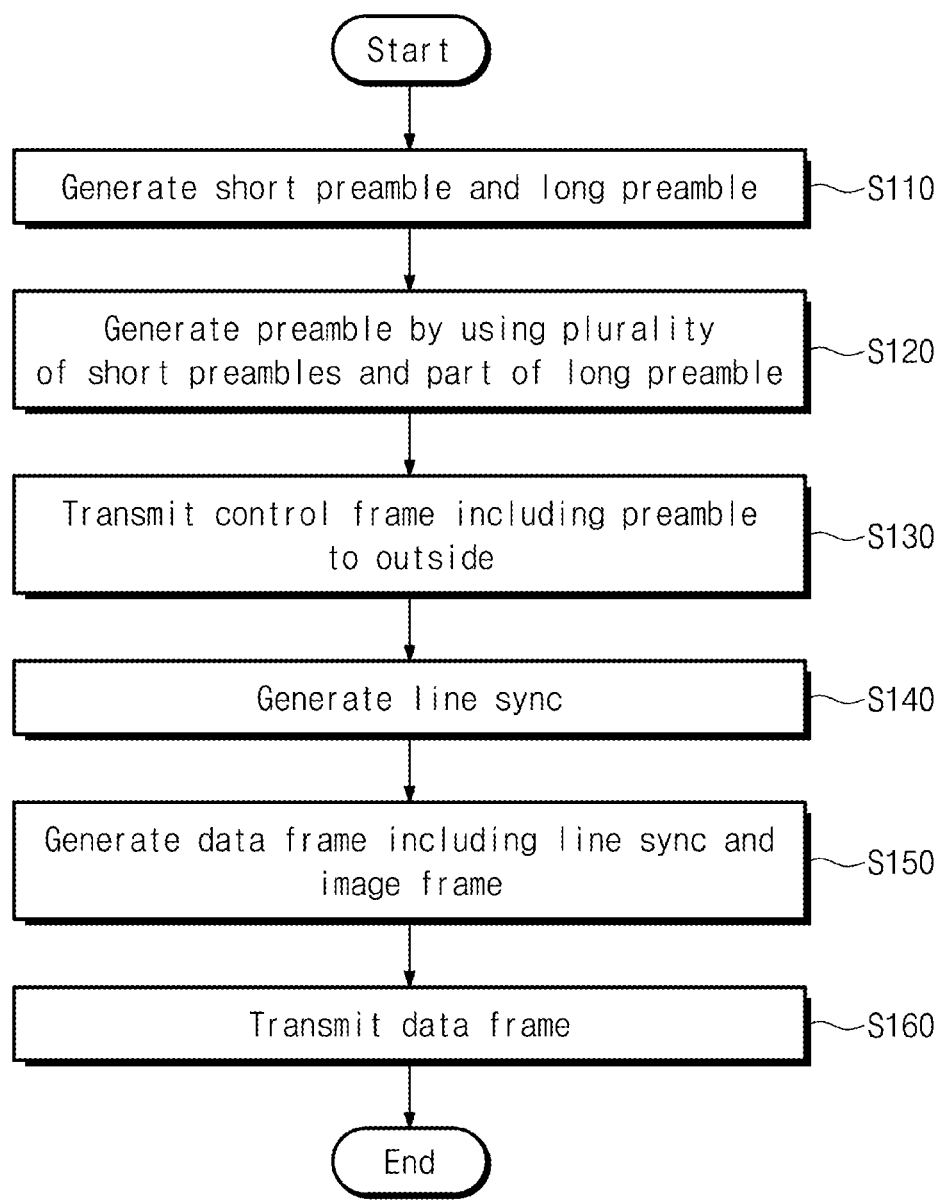
FIG. 10 is a flowchart illustrating an operation method of a capsule endoscope according to an embodiment of the inventive concept.

FIG. 10 is a flowchart illustrating an operation method of a capsule endoscope according to an embodiment of the inventive concept. To help understanding of the description, FIG. 1 and FIG. 2 will be described together.

In operation S110, a short preamble and a long preamble may be generated. For example, the short preamble and the long preamble may be generated by a pseudo-random number generator and a Manchester encoding, respectively, to have a predetermined number of bits.

In operation S120, a preamble may be generated based on the short preamble and the long preamble. For example, the preamble may include a plurality of short preambles (or at least one short preamble) and a part of a long preamble. That is, the long preambles included in each of the plurality of preambles may have different bit values. This allows what number a control frame is by analyzing the preamble.

In operation S130, the control frame including the preamble and the switching time may be transmitted to the outside. For example, the switching time may be a time required to select a selectable reception electrode pair among the plurality of reception electrodes 1210_1 to 1210_n. For example, each of the plurality of control frames may be transmitted to a selectable reception electrode pair among a plurality of reception electrodes.

In operation S140, a line sync may be generated. For example, the line sync may be generated by a pseudo-random number generator, a Manchester encoder, and a repeater to have a predetermined number of bits. A correlation value may be calculated using the bit values included in the line sync and the data frame may be synchronized based on the calculated correlation value. In addition, the sign of the calculated correlation value may be reflected to the sign value of the data frame to be transmitted later.

In operation S150, a data frame including a line sync and an image frame may be generated. The data frame may further include a header for enabling frame discrimination, and a CRC for error detection.

In operation S160, the data frame may be transmitted. For example, the data frame may be transmitted to the reception electrode pair that receives a control frame having the largest correlation value among the plurality of reception electrodes.

FIG. 11 is a flowchart illustrating an operation method of a capsule endoscope receiver according to an embodiment of the inventive concept. To help understanding of the description, FIG. 1 and FIG. 9 will be described together.

In operation S210, a plurality of control frames may be received. For example, each of the plurality of control frames may include a preamble and a switching time. Each preamble may include a plurality of short preambles (or at least one short preamble) and a part of a long preamble. For example, each of the plurality of control frames may be received through one pair of selectable reception electrodes among the plurality of reception electrodes.

In operation S220, a correlation value may be calculated using the preamble included in each control frame. For example, the preamble and line sync processor 1230 of the capsule endoscope receiver 1200 may calculate the correlation value of each preamble using the bit value of the preamble included in each control frame.

In operation S230, the reception electrode pair that receives a preamble having the largest correlation value may be selected. For example, the preamble and line sync processor 1230 may generate a switch control signal based on the calculated correlation value. Under the control of the switch control signal, the switching circuit 1222 may select the reception electrode pair that receives a preamble having the largest correlation value.

In operation S240, data frames may be received through the selected reception electrode pair. For example, each data frame may include a line sync, a header, data, and a CRC.

In operation S250, the correlation value may be calculated using the line sync included in the data frame. The sign of the calculated correlation value may be stored separately and the data frames may be synchronized based on the calculated correlation value.

In operation S260, the sign of the correlation value using the line sync may be reflected to the data frame. For example, as an XOR operation is performed on the header value, the data, and the CRC and the code value of the correlation value, it may be reflected to the sign of the data frame.

According to the above-described structure of the control frame, the preamble included in the control frame may include a plurality of short preambles and a part of a long preamble. Since the long preambles included in each control frame have different bit values, the long preamble may be distinguished from other control frames without a separate header. Therefore, the structure of the control frame may be simplified.

In addition, according to the structure of the above-described data frame, the line sync may be used to determine the sign value of the data frame changing in real time, and may be used to reflect it to a header, data, and a CRC.

According to an embodiment of the inventive concept, provided is a preamble used for selecting an optimal reception electrode pair that efficiently delivers a data frame to the outside of a human body.

In addition, according to an embodiment of the inventive concept, provided is a line sync used for efficiently evaluating a code value of changing data.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A capsule endoscope transmitter configured to transmit a structured frame including control frames and one or more data frames to a capsule endoscope receiver, the capsule endoscope transmitter comprising:

a short preamble generator configured to generate short preambles for synchronizing the control frames by encoding an output of a first pseudo-random number generator, the control frames being used to select a reception electrode pair that receives the structured frame;

a long preamble generator configured to generate a plurality of long preambles for identifying the control frames by encoding an output of a second pseudo-random number generator, each of the long preambles having different respective values;

a multiplexer configured to generate respective control frame preambles of the control frames, each control frame preamble of the control frame preambles comprising respective one or more of the short preambles and a respective one of the long preambles; and a line sync generator configured to generate a line sync for synchronizing the one or more data frames and identifying a code value of each of the one or more data frames, wherein the first pseudo-random number generator is different from the second pseudo-random number generator.

2. The capsule endoscope transmitter of claim 1, wherein the short preamble generator comprises:

the first pseudo-random number generator configured to a generate a pseudo-random number of a first bit value by using a first initial value; and a first Manchester encoder configured to perform Manchester encoding on an output of the first pseudo-random number generator.

3. The capsule endoscope transmitter of claim 2, wherein the first pseudo-random number generator is a 7 bit pseudo-random number generator, the first bit value is 128bits, and an output of the first Manchester encoder is 256 bits.

4. The capsule endoscope transmitter of claim 3, wherein a generator polynomial of the first pseudo-random number generator is $P(z)=z^7+z^6+1$, the first initial value is '1000000', and the first Manchester encoder encodes bit '0' to bits '01' and bit '1' to bits '10'.

5. The capsule endoscope transmitter of claim 1, wherein the long preamble generator comprises:

the second pseudo-random number generator configured to generate a pseudo-random number of a second bit value by using a second initial value; and a second Manchester encoder configured to produce the plurality of long preambles by Manchester encoding an output of the second pseudo-random number generator.

6. The capsule endoscope transmitter of claim 5, wherein the second pseudo-random number generator is a 12 bit pseudo-random number generator, the second bit value is 4096 bits, and an output of the second Manchester encoder is 8192 bits.

7. The capsule endoscope transmitter of claim 6, wherein a generator polynomial of the second pseudo-random number generator is $P(z)=z^{12}+z^{11}+z^8+z^6+1$, the second initial value is '100000000000', and the second Manchester encoder encodes bit '0' to bits '01' and bit '1' to bits '10'.

8. The capsule endoscope transmitter of claim 6, wherein if a number of the control frames is 30, each of the long preambles comprises 256 bit data.

9. The capsule endoscope transmitter of claim 1, wherein the line sync generator comprises:

a third pseudo-random number generator configured to generate a pseudo-random number of a third bit value by using a third initial value;

a third Manchester encoder configured to perform Manchester encoding on an output of the third pseudo-random number generator; and a repeater configured to repeat an output of the third Manchester encoder at least once.

10. The capsule endoscope transmitter of claim 9, wherein a generator polynomial of the third pseudo-random number generator is $P(z)=z^5+z^3+1$, the third initial value is '10000', and the third Manchester encoder encodes bit '0' to bits '01' and bit '1' to bits '10'.

11. A method of performing human body communication by using a capsule endoscope transmitter and a capsule endoscope receiver, the method comprising:

generating short preambles for synchronizing a plurality of control frames by encoding an output of a first pseudo-random number generator;

generating long preambles for identifying the plurality of control frames by encoding an output of a second pseudo-random number generator, each of the long preambles having different respective values;

generating the plurality of control frames respectively including a plurality of control frame preambles, each control frame preamble of the control frame preambles comprising at least one of the short preambles and a respective one of the long preambles; and generating a line sync for synchronizing a plurality of data frames transmitted subsequent to the plurality of control frames and identifying a sign value of each of the plurality of data frames, wherein the first pseudo-random number generator is different from the second pseudo-random number generator.

12. The method of claim 11, when the plurality of control frames are received, by the capsule endoscope receiver, further comprising:

calculating a correlation value of the long preamble included in each of the plurality of control frames; and selecting one reception electrode pair among a plurality of reception electrodes based on the correlation value of the long preamble.

13. The method of claim 12, when the plurality of data frames including a link sync and data are received through the selected reception electrode pair, further comprising:

calculating a correlation value by using the line sync including bits repeated at least twice;

synchronizing a data frame by using a correlation value of the line sync; and reflecting an XOR operation result for the data and a sign of the correlation value of the line sync to the data frame.

14. The method of claim 13, further comprising reflecting an XOR operation result for a header and a cyclic redundancy check (CRC) included in the data frame, and the sign of the correlation value of the line sync to the data frame.

15. The method of claim 11, wherein generating the short preambles comprises Manchester encoding an output of the first pseudo-random number generator; and wherein generating the long preambles comprises Manchester encoding the output of the second pseudo-random number generator.

16. The method of claim 11, wherein generating the line sync comprises:

Manchester encoding an output of a third pseudo-random number generator; and repeating the output of the Manchester encoding a plurality of times to generate the line sync.

* * * * *